(12) United States Patent
Dixon et al.

(10) Patent No.: US 9,877,905 B2
(45) Date of Patent: Jan. 30, 2018

(54) PERSONAL CARE COMPOSITION AND METHOD OF USE THEREOF

(71) Applicants: Nicholas John Dixon, Ellesmere Port (GB); Amy Helena Rigby, Ellesmere Port (GB); Debbie Lorraine Timmerman, Ellesmere Port (GB)

(72) Inventors: Nicholas John Dixon, Ellesmere Port (GB); Amy Helena Rigby, Ellesmere Port (GB); Debbie Lorraine Timmerman, Ellesmere Port (GB)

(73) Assignee: INNOSPEC LIMITED, Cheshire (GB)

( * ) Notice: Subject to any disclaimer, the term of this patent is extended or adjusted under 35 U.S.C. 154(b) by 0 days.

(21) Appl. No.: 14/366,830

(22) PCT Filed: Dec. 20, 2012

(86) PCT No.: PCT/GB2012/053207
§ 371 (c)(1),
(2) Date: Jun. 19, 2014

(87) PCT Pub. No.: WO2013/093475
PCT Pub. Date: Jun. 27, 2013

(65) Prior Publication Data
US 2015/0139929 A1 May 21, 2015

(30) Foreign Application Priority Data

Dec. 22, 2011 (GB) .................. 1122195.9

(51) Int. Cl.
A61K 8/46 (2006.01)
A61Q 5/02 (2006.01)
C11D 1/12 (2006.01)
C11D 17/00 (2006.01)

(52) U.S. Cl.
CPC ............. *A61K 8/466* (2013.01); *A61Q 5/02* (2013.01); *C11D 1/126* (2013.01); *C11D 17/006* (2013.01)

(58) Field of Classification Search
None
See application file for complete search history.

(56) References Cited

U.S. PATENT DOCUMENTS

| 2,894,912 | A | | 7/1959 | Geitz |
| 3,958,581 | A | | 5/1976 | Abegg et al. |
| 3,962,418 | A | | 6/1976 | Birkofer |
| 4,009,256 | A | | 2/1977 | Nowak, Jr. et al. |
| 4,275,055 | A | | 6/1981 | Nachtigal et al. |
| 5,743,388 | A | * | 4/1998 | Kerr et al. .................. 206/77.1 |
| 6,559,110 | B1 | * | 5/2003 | Lopes .................. A61K 8/23 424/44 |
| 7,709,431 | B2 | * | 5/2010 | Mercurio .............. A61K 8/046 424/70.1 |
| 2008/0234159 | A1 | * | 9/2008 | Anantaneni ........... A61K 8/466 510/129 |
| 2009/0082245 | A1 | * | 3/2009 | Smith ..................... C11D 7/10 510/336 |

FOREIGN PATENT DOCUMENTS

| EP | 530974 A1 | 3/1993 |
| GB | 954833 A | 4/1964 |
| KR | 1020040013228 | 2/2014 |
| WO | 94/09763 A1 | 5/1994 |
| WO | 95022311 A1 | 8/1995 |
| WO | 2005022311 A1 | 8/1995 |
| WO | 96031188 A1 | 10/1996 |
| WO | 2006031188 A1 | 10/1996 |
| WO | 2005075623 A1 | 8/2005 |
| WO | 2007/130390 A2 | 11/2007 |

OTHER PUBLICATIONS

OUCC, Sodium Isethionate, retrieved online on Jun. 29, 2016.*
Chembook, Sodium Isethionate, http://www.chemicalbook.com/ProductMSDSDetailCB8253893_EN.htm, retrieved online on May 19, 2015.*
International Search Report for International Application No. PCT/GB2012/053207 dated May 2, 2013.
Gough, T. "Sulfate-Free Made Easy: Rationale and Guide to Formulating Highly Appealing Sulfate-Free Personal Care Compositions." Copyright Innospec, Ltd. (Jun. 6, 2012), retrieved from www.in-cosmetics.com.
International Preliminary Report on Patentability dated Jul. 3, 2014 for PCT/GB12/53207.

* cited by examiner

*Primary Examiner* — Jennifer A Berrios
(74) *Attorney, Agent, or Firm* — Burns & Levinson LLP; Janine M. Susan

(57) ABSTRACT

A solid personal care composition comprising at least 60 wt % of one or more solid surfactants of which at least 10 wt % comprises one or more compounds of formula (I) wherein $R^1$ represents a $C_{4-36}$ substituted or unsubstituted hydrocarbyl group; each of $R^2$, $R^3$, $R^4$ and $R^5$ independently represents a hydrogen atom or a $C_{1-4}$ alkyl group and wherein at least one of $R^2$, $R^3$, $R^4$ and $R^5$ is not hydrogen; and M+ represents a cation.

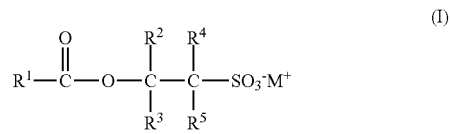

(I)

14 Claims, No Drawings

PERSONAL CARE COMPOSITION AND METHOD OF USE THEREOF

CROSS-REFERENCE TO RELATED APPLICATIONS

This application is a U.S. national stage application under 35 U.S.C., 371 of co-pending International Application No. PCT/GB2012/053207 filed on Dec. 20, 2012 and entitled COMPOSITION AND METHOD, which in turn claims priority to Great Britain Patent Application No. 1122195.9, filed on Dec. 22, 2011, which is incorporated by reference herein in its entirety for all purposes.

The present invention relates to personal care compositions, especially shampoo compositions. In particular the invention relates to solid shampoo compositions.

Many commonly available shampoo compositions are in the form of viscous liquid compositions. However these compositions are heavy and often contain large volumes of water. A user will often pour a much larger volume than they intended of the composition onto their hand prior to application to the hair and thus significant quantities are wasted. It is also expensive and environmentally unfriendly to transport large volumes of liquid.

Solid shampoo formulations offer significant advantages over liquid compositions. They are more compact and easy to transport. In addition a user typically only uses the amount of shampoo needed and thus there is a reduction in waste.

Solid shampoo compositions known in the art are largely sulfate-surfactant based. These have the desired shampoo properties of providing good foam or lather and rinse well from the hair. However a disadvantage of high-sulfate shampoo compositions is that sulfates are known to be degreasing and may feel harsh on the skin or the hair. They are also known to strip colour from dyed hair. Thus reducing the level of sulfates present in such compositions would be desirable.

It is an aim of the present invention to provide an improved solid shampoo formulation.

According to a first aspect of the present invention there is provided a solid personal care composition comprising at least 60 wt % of one or more solid surfactants of which at least 10 wt % comprises one or more compounds of formula (I):

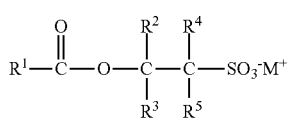

wherein $R^1$ represents a $C_{4-36}$ substituted or unsubstituted hydrocarbyl group;

each of $R^2$, $R^3$, $R^4$ and $R^5$ independently represents a hydrogen atom or a $C_{1-4}$ alkyl group and wherein at least one of $R^2$, $R^3$, $R^4$ and $R^5$ is not hydrogen; and $M^+$ represents a cation.

For the avoidance of doubt, the compositions of the present invention comprise at least 60 wt % of one or more solid surfactants. Of this 60 wt %, at least 10 wt % comprises one or more compounds of formula (I).

By solid surfactants we mean to refer to compounds which are in the solid state under normal atmospheric conditions (i.e. at a pressure of 1 atmosphere and 298 K).

Preferably the composition of the present invention comprises at least 65 wt % solid surfactants, preferably at least 70 wt %, more preferably at least 72 wt %, preferably at least 75 wt %, suitably at least 78 wt %, for example at least 80 wt %.

In this specification, unless otherwise indicated any amounts referred to relate to the amount of active component present in the composition. The skilled person will appreciate that commercial sources of some of the components referred to herein may include impurities, side-products and/or residual starting material. However the amounts specified refer only to the active material and do not include any impurity, side-product, starting material or diluent that may be present.

At least 10 wt % of the solid surfactants present in the compositions of the invention comprises one or more compounds of formula (I). Preferably at least 15 wt % of the solid surfactants present in the composition comprises one or more compounds of formula (I), suitably at least 20 wt %, preferably at least 25 wt %, for example at least 30 wt % or at least 35 wt %. In some embodiments at least 40 wt % of the solid surfactants comprises one or more compounds of formula (I), suitably at least 45 wt %, preferably at least 50 wt %, more preferably at least 55 wt %, suitably at least 60 wt %, preferably at least 65 wt %, for example at least 70 wt %. The solid surfactants may comprises at least 75 wt % of one or more compounds of formula (I), for example at least 80 wt %, suitably at least 85 wt %, at least 90 wt % or at least 95 wt %. In some embodiments substantially all of the solid surfactant compounds present in the composition of the present invention may comprise compounds of formula (I).

In some embodiments only a single compound of formula (I) may be present. In some embodiments a mixture of two or more compounds of formula (I) may be present. In such embodiments the above amounts refer to the total amounts of all compounds of formula (I) present in the composition.

The composition of the present invention comprises one or more compounds of formula (I):

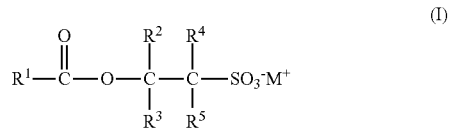

Preferably $R^1$ is selected from a substituted or unsubstituted alkyl, alkenyl, aryl or alkylaryl group. More preferably $R^1$ is selected from a substituted or unsubstituted alkyl or alkenyl group. Most preferably $R^1$ is an unsubstituted alkyl or alkenyl group, especially an unsubstituted alkyl group.

Preferably $R^1$ represents a $C_{5-30}$ alkyl group, preferably a $C_{7-24}$ alkyl group, more preferably a $C_{7-21}$ alkyl group, most preferably a $C_{7-17}$ alkyl group.

Preferably $R^2$ represents a $C_{1-4}$ alkyl group, suitably a $C_{1-4}$ alkyl group in which a propyl or butyl group, when present, is straight-chained. Preferably $R^2$ represents an n-propyl, ethyl or, most preferably, a methyl group.

Preferably $R^3$ represents a hydrogen atom.

Preferably one of $R^4$ and $R^5$ represents a hydrogen atom and the other represents a hydrogen atom or a $C_{1-4}$ alkyl group. Preferably one of $R^4$ and $R^5$ represents a hydrogen atom or a $C_{1-4}$ alkyl group in which a propyl or butyl group is straight-chain. Preferably one of $R^4$ and $R^5$ represents an n-propyl, ethyl or methyl group or, most preferably, a hydrogen atom. Most preferably both $R^4$ and $R^5$ represent hydrogen atoms.

In some embodiments the composition of the present invention may include a mixture of more than one compound of formula (I). For example an isomeric mixture of compounds of formula (I) may be present. Such a mixture may include, for example a compound in which $R^2$ is alkyl (suitably methyl) and $R^3$, $R^4$ and $R^5$ are all hydrogen and a compound in which $R^5$ is alkyl (suitably methyl) and $R^2$, $R^3$ and $R^4$ are all hydrogen.

Preferably $M^+$ represents an optionally substituted ammonium cation or, most preferably, a metal cation. Suitable ammonium cations include $NH_4^+$ and the ammonium cation of triethanolamine. Suitable metal cations include alkali metal cations, for example sodium, lithium and potassium cations, and alkaline earth metal cations, for example calcium and magnesium cations. Preferably $M^+$ represents a zinc, potassium or sodium cation. Most preferably $M^+$ represents a sodium cation.

The skilled person will appreciate that when $M^+$ is a divalent metal cation two moles of anion will be present for each mole of cation.

$R^1$ may be an alkyl group or an alkenyl group. Preferably $R^1$ is an alkyl group. In some embodiments the component surfactant of the present invention may comprise a mixture of fatty acids to form a mixture of compounds of formula (I) in which $R^1$ may be different.

$R^1$ is preferably the residue of a fatty acid. Fatty acids obtained from natural oils often include mixtures of fatty acids. For example the fatty acid obtained from coconut oil contains a mixture of fatty acids including $C_{12}$ lauric acid, $C_{14}$ myristic acid, $C_{16}$ palmitic acid, $C_5$ caprylic acid, and $C_{18}$ stearic and oleic.

$R^1$ may include the residue of one or more naturally occurring fatty acids and/or of one or more synthetic fatty acids. In some preferred embodiments $R^1$ consists essentially of the residue of a single fatty acid.

Examples of carboxylic acids from which $R^1$ may be derived include coco acid, butyric acid, hexanoic acid, caproic acid, caprylic acid, capric acid, lauric acid, myristic acid, palmitic acid, palmitoleic acid, stearic acid, oleic acid, linoleic acid, arachidic acid, gadoleic acid, arachidonic acid, eicosapentaenoic acid, behinic acid, eruic acid, docosahexanoic lignoceric acid, naturally occurring fatty acids such as those obtained from coconut oil, tallow, palm kernel oil, butterfat, palm oil, olive oil, corn oil, linseed oil, peanut oil, fish oil and rapeseed oil; synthetic fatty acids made as chains of a single length or a selected distribution of chain lengths; and mixtures thereof. Most preferably $R^1$ comprises the residue of lauric acid, that is a saturated fatty acid having 12 carbon atoms or the residue of mixed fatty acids derived from coconut oil.

The compound of formula (I) may be prepared by any of the methods disclosed in the prior art, for example see the methods described in WO94/09763 and WO2005/075623.

In especially preferred embodiments, $R^3$, $R^4$ and $R^5$ are all hydrogen and $R^2$ is ethyl or, most preferably methyl.

In preferred embodiments the compound of formula (I) is the reaction product of sodium methyl isethionate and a fatty acid, that is a compound of formula $R^1COOCHR^2CHR^4SO_3^-M^+$ in which one of $R^2$ and $R^4$ is methyl and the other is hydrogen. Mixtures of these isomers may be present.

In especially preferred embodiments the composition comprises a mixture of isomers, that is a compound of formula $R^1COOCH_2CHR^4SO_3^-M^+$ in which $R^4$ is alkyl (preferably methyl) and a compound of formula $R^1COOCHR^2CH_2SO_3^-M^+$ in which $R^2$ is alkyl (preferably methyl).

In some embodiments the composition of the present invention comprises one or more of sodium lauroyl methyl isethionate, sodium cocoyl methyl isethionate and sodium oleoyl methyl isethionate.

Most preferably the composition of the present invention comprises sodium lauroyl methyl isethionate and/or sodium cocoyl methyl isethionate. Sodium lauroyl methyl isethionate is especially preferred.

In some embodiments the composition of the present invention comprises one or more further solid surfactants in addition to the surfactants of formula (I).

Other solid surfactants of the present invention may be selected from anionic surfactants, cationic surfactants, non-ionic surfactants and amphoteric surfactants.

Suitable anionic surfactants for use in the composition of the present invention include salts of $C_{12}$ to $C_{18}$ carboxylic acids, ethoxylated carboxylic acids, ester carboxylates and ethoxylated ester carboxylates and sarcosinates. Other suitable anionic surfactants include sulfates and sulfonates, for example alkyl sulfates, alkyl ether sulfates, alcohol sulfates, alcohol ether sulfates, α-olefin sulfonates, linear alkyl sulfonates; and phosphate esters.

Suitable anionic surfactants may be selected from salts of fatty acids; alkali metal salts of mono- or dialkyl sulfates; mono- or dialkyl ether sulfates; lauryl ether sulfates; alkyl sulfonates; alkyl aryl sulfonates; primary alkane disulfonates; alkene sulfonates; hydroxyalkane sulfonates; alkyl glyceryl ether sulfonates; alpha-olefinsulfonates; alkyl phosphates; sulfonates of alkylphenolpolyglycol ethers; salts of alkyl sulfopolycarboxylic acid esters; alkyl sulfosuccinates and salts thereof, alkyl ether sulfosuccinates and salts thereof, non-acylated alkyl isethionates; fatty acid taurates; acyl taurates; products of condensation of fatty acids with oxy- and aminoalkanesulfonic acids; sulfated derivatives of fatty acids and polyglycols; alkyl and acyl sarcosinates; sulfoacetates; alkyl phosphates; alkyl phosphate esters; acyl lactates; alkanolamides of sulfated fatty acids and salts of lipoamino acids. Particularly exemplary salts of the above, where applicable, are the sodium, potassium, ammonium, magnesium and triethanolamine salts.

Preferred additional anionic detersive surfactants for use in the present invention include alkyl glyceryl ether sulfonate, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and combinations thereof.

Particularly preferred anionic surfactants for use herein include sodium methyl cocoyl taurate, sodium lauryl sarcosinate, alkyl sulfates, for example sodium lauryl sulfate and alkyl ether sulfates, for example sodium lauryl ether sulfate.

Suitable non-ionic surfactants for use herein include alcohol ethoxylates and ethylene oxide/propylene oxide copolymer derived surfactants, sugar esters, especially sorbitan esters, alkyl polyglucosides, fatty acid ethoxylates or polyethylene glycol esters and partial esters, alkanolamides and amineoxides.

Especially preferred non-ionic surfactants for use herein include fatty acid alkanolamides, ethylene glycol stearate and ethylene glycol distearate.

Suitable non-ionic surface-active agents may be selected from the following: reaction products of compounds having a hydrophobic group and a reactive hydrogen atom, for example aliphatic alcohols, acids, amides or alkyl phenols with alkylene oxides, especially ethylene oxide either alone or with propylene oxide (for example alkyl ($C_6$-$C_{22}$) phenolethylene oxide condensates, the condensation products of aliphatic ($C_8$-$C_{15}$) primary or secondary linear or branched alcohols with ethylene oxide, and products made by condensation of ethylene oxide with the reaction products of propylene oxide and ethylenediamine); long chain tertiary amine oxides, long chain tertiary phosphine oxides and dialkyl sulfoxides; alkyl amine oxides, alkyl amido amine oxides; alkyl tertiary phosphine oxides; alkoxyl alkyl amines; sorbitan; sorbitan esters; sorbitan ester alkoxylates; glycerol ester alkoxylates; sucrose esters; sugar amides, such as a polysaccharide amide; lactobionamides; and alkyl polysaccharide nonionic surfactants, for example alkylpolyglycosides. Preferred non-ionic surfactants are sucroglycerides and ethoxylated fatty alcohols, especially those derived from lauryl, cetylstearyl, stearyl, cetyl and oleocetyl alcohols.

Suitable cationic surfactants for use herein are typically based on fatty amine derivates or phosphonium quaternary ions, and quaternary ammonium compounds.

Suitable cationic surfactants for use herein include tertiary amine salts, mono alkyl trimethyl ammonium chloride, mono alkyl trimethyl ammonium methyl sulfate, dialkyl dimethyl ammonium chloride, dialkyl dimethyl ammonium methyl sulfate, trialkyl methyl ammonium chloride and trialkyl methyl ammonium methyl sulfate.

Some especially preferred cationic surfactants for use herein are monoalkyl quaternary ammonium compounds in which the alkyl chain length is C16 to C22.

Examples of suitable cationic surfactants include quaternary ammonium compounds, particularly trimethyl quaternary compounds.

Preferred quaternary ammonium compounds include cetyltrimethylammonium chloride, behenyltrimethylammonium chloride (BTAC), cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, PEG-2 oleylammonium chloride and salts of these where the chloride is replaced by halogen, (e.g., bromide), acetate, citrate, lactate, glycolate, phosphate nitrate, sulfate, or alkylsulfate.

Further suitable cationic surfactants include those materials having the CTFA designations Quaternium-5, Quaternium-31 and Quaternium-18. Mixtures of any of the foregoing materials may also be suitable. A particularly useful cationic surfactant for use as a hair conditioning agent is cetyltrimethylammonium chloride, available commercially, for example as GENAMIN CTAC, ex Hoechst Celanese.

Salts of primary, secondary, and tertiary fatty amines are also suitable cationic surfactants. The alkyl groups of such amines preferably have from 12 to 22 carbon atoms, and can be substituted or unsubstituted.

Useful cationic surfactants include amido substituted tertiary fatty amines, in particular tertiary amines having one C12 to C22 alkyl or alkenyl chain. Such amines include stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide.

Also useful are dimethylstearamine, dimethylsoyamine, soyamine, myristylamine, tridecylamine, ethylstearylamine, Ntallowpropane diamine, ethoxylated (with 5 moles of ethylene oxide) stearylamine, dihydroxyethylstearylamine, and arachidyl behenylamine.

These amines are typically used in combination with an acid to provide the cationic species. Suitable acids include L-glutamic acid, lactic acid, hydrochloric acid, malic acid, succinic acid, acetic acid, fumaric acid, tartaric acid, citric acid, L-glutamic hydrochloride, and mixtures thereof; more preferably L-glutamic acid, lactic acid, citric acid.

Other useful cationic amine surfactants include those disclosed in U.S. Pat. No. 4,275,055.

Suitable amphoteric surfactants include those based on fatty nitrogen derivatives and those based on betaines.

Suitable amphoteric or zwitterionic surfactants may be selected from betaines, for example alkyl betaines, alkylamidopropyl betaines, alkylamidopropyl hydroxy sultaines, alkylamphoacetates, alkylamphodiacetates, alkylamphopropionates, alkylamphodipropionates, alkyliminodipropionates and alkyliminodiacetate.

Amphoteric or zwitterionic surfactants for use in the compositions of the present invention may include those which have an alkyl or alkenyl group of 7 to 22 carbon atoms and comply with an overall structural formula:

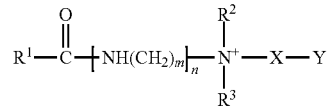

where $R^1$ is alkyl or alkenyl of 7 to 22 carbon atoms; $R^2$ and $R^3$ are each independently alkyl, hydroxyalkyl or carboxyalkyl of 1 to 6 carbon atoms; m is 2 to 4; n is 0 or 1; X is alkylene of 1 to 6 carbon atoms optionally substituted with hydroxyl; and Y is $-CO_2$ or $-SO_3$.

Amphoteric or zwitterionic surfactants may include simple betaines of formula:

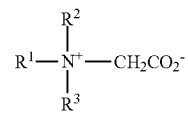

and amido betaines of formula:

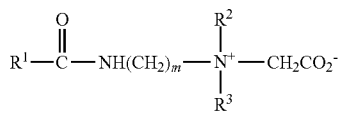

where m is 2 or 3.

In both formulae $R^1$, $R^2$ and $R^3$ are as defined previously. $R^1$ may, in particular, be a mixture of $C_{12}$ and $C_{14}$ alkyl groups derived from coconut so that at least half, preferably at least three quarters, of the groups $R^1$ has 10 to 14 carbon atoms. $R^2$ and $R^3$ are preferably methyl.

Amphoteric or zwitterionic surfactants may include sulfobetaines of formula:

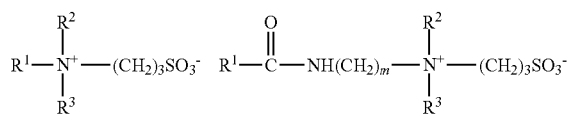

where m is 2 or 3, or variants of these in which $-(CH_2)_3SO_3^-$ is replaced by

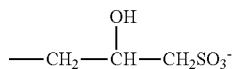

where $R^1$, $R^2$ and $R^3$ in these formulae are as defined previously.

Amphoteric or zwitterionic surfactants may include amphoacetates and diamphoacetates. Amphoacetates generally conform to the following formula:

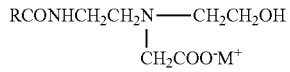

Diamphoacetates generally conform to the following formula:

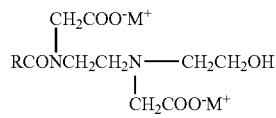

where R is an aliphatic group of 8 to 22 carbon atoms and M is a cation such as sodium, potassium, ammonium, or substituted ammonium.

Suitable acetate-based surfactants include lauroamphoacetate; alkyl amphoacetate; cocoampho(di)acetate; cocoamphoacetate; disodium cocoamphodiacetate; sodium cocoamphoacetate; disodium cocoamphodiacetate; disodium capryloamphodiacete; disodium lauroamphoacetate; sodium lauroamphoacetate and disodium wheatgermamphodiacetate.

Suitable betaine surfactants include alkylamido betaine; alkyl betaine, $C_{12/14}$ alkyldimethyl betaine; cocoamidopropylbetaine; tallow bis(hydroxyethyl) betaine; hexadecyldimethylbetaine; cocodimethylbetaine; alkyl amido propyl sulfo betaine; alkyl amino betaine; coco amido propyl dimethyl betaine; alkyl amido propyl dimethyl amine betaine; cocamidopropyl betaine; lauryl betaine; laurylamidopropl betaine, coco amido betaine, lauryl amido betaine, alkyl amino betaine; alkyl amido betaine; coco betaine; lauryl betaine; diemethicone propyl PG-betaine; oleyl betaine; N-alkyldimethyl betaine; coco biguamide derivative, $C_8$ amido betaine; $C_{12}$ amido betaine; lauryl dimethyl betaine; alkylamide propyl betaine; amido betaine; alkyl betaine; cetyl betaine; oleamidopropyl betaine; isostearamidopropyl betaine; lauramidopropyl betaine; 2-alkyl-N-carboxymethyl-N-hydroxyethyl imidazolinium betaine; 2-alkyl-N-carboxyethyl-N-hydroxyethyl imidazolinium betaine; 2-alkyl-N-sodium carboxymethyl-N-carboxymethyl oxyethyl imidazolinium betaine; N-alkyl acid amidopropyl-N,N-dimethyl-N-(3-sulfopropyl)-ammonium-betaine; N-alkyl-N,N-dimethyl-N-(3-sulfopropyl)-ammonium-betaine; cocodimethyl betaine; apricotamidopropyl betaine; isostearamidopropyl betaine; myristamidopropyl betaine; palmitamidopropyl betaine; cocamidopropyl hydroxyl sultaine; undecylenamidopropyl betaine; cocoamidosulfobetaine; alkyl amido betaine; $C_{12/18}$ alkyl amido propyl dimethyl amine betaine; lauryldimethyl betaine; ricinol amidobetaine; tallow aminobetaine.

Suitable glycinate surfactants include cocoamphocarboxyglycinate; tallowamphocarboxygycinate; capryloamphocarboxyglycinate, oleoamphocarboxyglycinate, bis-2-hydroxyethyl tallow glycinate; lauryl amphoglycinate; tallow polyamphoglycinate; coco amphoglycinate; oleic polyamphoglycinate; $N-C_{10/12}$ fatty acid amidoethyl-N-(2-hydroxyethyl)-glycinate; $N-C_{12/18}$-fatty acid amidoethyl-N-(2-hydroxyethyl)-glycinate; dihydroxyethyl tallow glycinate.

Some preferred surfactants for use herein include sodium lauryl sulfate, sodium lauryl ether sulfate (2EO); alkanolamides for example cocodiaethanolamide; triethanol amine lauryl sulfate; sodium laureth-2 sulfate; imidazoline derived surfactants; lauric sorbitan ester 20EO; quaternary hydrolysed proteins, dimethicone copolyol; lanolin derivates; and cationic guar gum derivates. Suitable surfactants for use herein include sodium laurylsulfate and other alkyl sulfates and ether sulfates as well as sulfosuccinates, amine oxides, sodium laurethcarboxylates, sodium lauroylsarcosinates and amphoteric cocoamidopropyl betaine, sodium amphocarboxyglycinate and alkylpolyamino carboxylates.

Suitably the composition may comprise from 0.1 to 10 wt %, suitably from 0.5 to 7.5 wt %, for example from 1 to 5 wt % or from 2 to 4 wt % of an amphoteric surfactant. Suitable amphoteric surfactants are betaines, for example cocoamidopropyl betaine.

Suitably the composition may comprise from 0.1 to 12 wt %, suitably 0.25 to 10 wt %, preferably 0.5 to 7.5 wt %, suitably from 1 to 5 wt % one or more anionic surfactants. Suitable anionic surfactants include taurates.

Suitably the composition comprises from 0.1 to 10 wt %, preferably 0.5 to 5 wt %, suitably 1 to 3 wt % of a taurate surfactant, for example sodium methyl cocoyl taurate.

The composition of the present invention may comprise a chelating agent. Suitable chelating agents include ethylenediamine-N,N'-disuccinic acid, methylglycinediacetic acid, glutamic acid N,N-diacetic acid, imino disuccinic acid, diethylene triamine pentaacetic acid, ethylenediamine tetraacetic acid, diethylenetriamine penta methylene phosphonic acid, etidronic acid and anions and mixtures thereof.

Preferred chelants are biodegradable chelants for example ethylenediamine-N,N'-disuccinic acid, methylglycinediacetic acid, glutamic acid N,N-diacetic acid, imino disuccinic acid and anions and mixtures thereof.

Suitably the composition comprises from 0.1 to 5 wt %, suitably from 0.5 to 2 wt % of a chelating agent. One especially preferred chelating agent is trisodium ethylenediamine disuccinate.

In some preferred embodiments the compositions of the present invention comprise less than 10 wt % of isethionate ester compounds of formula $R^6COOCH_2CH_2SO_3^-M^+$ wherein $R^6$ is a substituted or unsubstituted alkyl or alkenyl groups having 4 to 36 carbon atoms.

Preferably the composition of the present invention comprise less than 5 wt % isethionate ester compounds of formula $R^6COOCH_2CH_2SO_3^-M^+$, more preferably less than 2.5 wt %, suitably less than 1 wt %. In some embodiments the compositions of the present invention are substantially free from isethionate ester compounds of formula $R^6COOCH_2CH_2SO_3^-M^+$.

Preferably the compositions of the present invention comprise less than 10 wt % traditional soap compounds. By traditional soap compounds we mean to refer to compounds commonly known as soap, i.e. the alkali metal and alkanol ammonium salts of aliphatic alkane or alkene monocarboxylic acids.

Preferably the compositions of the present invention comprise less than 5 wt % traditional soap compounds, preferably less than 2.5 wt %, more preferably less than 1 wt % traditional soap compounds. In some embodiments the compositions of the present invention may be substantially free from traditional soap compounds.

By substantially free from traditional soap compounds we mean that such a product is not deliberately added to the composition. However the skilled person will appreciate that fatty acids and salts thereof may be present in the composition as side products when providing other surfactants present in the composition, for example the compound of formula (I).

In some embodiments the compositions of the present invention may comprise from 1 to 75 wt % sulfate surfactants, for example from 1 to 50 wt %, suitably from 1 to 25 wt %.

In some embodiments the compositions of the present invention comprise less than 10 wt % sulfate surfactants, preferably less than 5 wt %, suitably less than 2.5 wt %, preferably less than 1 wt %.

By sulfate surfactants we mean to refer to compounds of formula $R^7OSO_3^-M^+$ where $R^7$ is a $C_4$ to $C_{36}$ alkyl or alkenyl group and M+ is an ammonium or metal ion, preferably a sodium ion.

The composition of the present invention may suitably comprise a conditioning agent. Suitable conditioning agents include cationic surfactants, cationic polymers and silicone conditioning agents. Suitable cationic surfactants are as previously defined herein.

Suitable cationic conditioning polymers include copolymers of 1-vinyl-2-pyrrolidine and 1-vinyl-3-methylimidazolium salt (CTFA name Polyquaternium-16); copolymers of 1-vinyl-2-pyrrolidine and dimethylaminoethyl methacrylate, (CTFA name Polyquaternium-11); cationic diallyl quaternary ammonium-containing polymers in particular (CTFA Polyquaternium 6 and Polyquaternium 7, mineral acid salts of amino-alkyl esters of homo- and copolymers of unsaturated carboxylic acids, for example as described in U.S. Pat. No. 4,009,256; and cationic polyacrylamides, for example as described in WO95/22311.

Cationic polysaccharide polymers suitable for use in compositions of the invention include those with an anhydroglucose residual group, such as a starch or cellulose. Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other suitable cationic polysaccharide polymers include quaternary nitrogen-containing cellulose ethers (e. g. as described in U.S. Pat. No. 3,962,418), and copolymers of etherified cellulose and starch (e. g. as described in U.S. Pat. No. 3,958,581).

A particularly suitable type of cationic polysaccharide polymer that can be used is a cationic guar gum derivative, such as guar hydroxypropyltrimonium chloride (commercially available from Rhone-Poulenc in their JAGUAR trademark series). Particularly preferred cationic polymers are JAGUAR C13S, JAGUAR C14, JAGUAR C15, JAGUAR C17 and JAGUAR C16 Jaguar CHT and JAGUAR C162.

A preferred cationic polymer is Polyquaternium-7, which comprises copolymers of acrylamide and diallyldimethyl ammonium chloride.

The compositions of the invention can contain silicone conditioning agents.

Suitable silicones include polydiorganosiloxanes, in particular polydimethylsiloxanes that have the CTFA designation dimethicone. Also suitable for use in compositions of the invention (particularly shampoos and conditioners) are polydimethyl siloxanes having hydroxyl end groups, which have the CTFA designation dimethiconol. Also suitable for use in compositions of the invention are silicone gums having a slight degree of cross-linking, for example as described in WO 96/31188.

A further preferred class of silicones for inclusion in shampoo bars of the invention are amino functional silicones. By "amino functional silicone" is meant a silicone containing at least one primary, secondary or tertiary amine group, or a quaternary ammonium group.

Examples of suitable amino functional silicones include: polysiloxanes having the CTFA designation "amodimethicone", Specific examples of amino functional silicones suitable for use in the invention are the aminosilicone oils DC2-8220, DC2-8166, DC2-8466, and DC2-8950-114 (all ex Dow Corning), and GE 1149-75, (ex General Electric Silicones).

Suitable quaternary silicone polymers are described in EP530974. A preferred quaternary silicone polymer is K3474, ex Goldschmidt.

Also suitable are emulsions of amino functional silicone oils with non-ionic and/or cationic surfactant.

Pre-formed emulsions of amino functional silicone are also available from suppliers of silicone oils such as Dow Corning and General Electric. Specific examples include DC929 Cationic Emulsion, DC939 Cationic Emulsion, and the non-ionic emulsions DC2-7224, DC2-8467, DC2-8177 and DC2-8154 (all ex Dow Corning).

The compositions of the present invention may include free fatty acids. These may be present in an amount of up to 10 wt %, for example up to 7 wt %.

The composition of the present invention may include salts of fatty acids for example salts of monovalent and/or divalent metals.

Free fatty acids and salts of fatty acids may be provided with the compound of formula (I) as side products.

The composition may contain up to 15 wt %, for example up to 10 wt % of a compound of formula $HOCHR^7CHR^8SO_3^-M^+$ wherein $R^7$ and $R^8$ is each hydrogen or alkyl (preferably methyl) provided at least one is not hydrogen.

The composition may include further optional ingredients for example fragrances, dyes, hair colourants such as semi-permanent dyes or pigments, hair growth agents, hair growth retardation agents, structuring aids, fillers, slipping agents, plasticising agents, anti-shrinkage agents, binding agents, agents to reduce solubility of the bar to prevent bar mushiness, flowing agents (to aid in processing before compressing into solid bars), disintegrants (to aid the dissolution of particularly robust bars), moisturisers, sensory property agents such as cooling agents and warming agents, scalp exfoliant particles, beads or encapsulates which are physically robust in the solid form but rupture on contact with water, hair styling agents which reside on the hair after rinsing to give the hair stylability and shape longevity, agents for the treatment and/or prevention of head and or pubic lice, agents for the eradication and/or repellence of ticks and other insect pets in human hair and/or animal hair/fur, fungicidal agents, bacteriocidal agents, yeasticidal agents, pH adjustment agents, chelating agents, antidandruff agents and conditioning agents. Components of this type are not limited to those mentioned and will be well known to the person skilled in the art.

Because the composition of the present invention is in the form of a solid it offers a number of advantages, especially in terms of its portability. Unlike liquid compositions the solid compositions of the present invention will not spill and damage other products in a bag or suitcase. As they do not contain the high volumes of water typically found in liquid compositions a much smaller volume of product is needed to achieve the same results. In addition solid compositions can usually be included in aircraft hand baggage without restrictions.

As well as being highly portable, the composition of the present invention offers a number of further beneficial properties. The composition has been found to be mild to the skin and hair. The compositions foam easily and provide a good lather and can be easily rinsed from the hair and skin. Hair treated using the composition is easy to comb and is soft and shiny.

The composition of the present invention is a personal care composition. Suitably it is a shampoo and/or body wash composition. Preferably it is a shampoo composition.

The composition of the present invention is a solid composition. Suitably the composition is provided in an easy to handle form that is acceptable to consumers.

In some embodiments the compositions may be provided as a bar of block, having an appearance similar to a bar of soap.

In some embodiments the composition may be provided with a cover. Such a cover may be easily opened to reveal all or part of the composition. Such a cover may help prevent the composition from being washed away between uses.

In some embodiments the composition may be provided in unit size portions suitable for a single use. Thus the composition may be provided as one or more discs, spheres or other shaped portions. Such single use portions have high consumer appeal as they enable a user to carry only the amount of product necessary if they are for example going away on a short trip.

According to a second aspect of the present invention there is provided a personal care product comprising the composition of the present invention and packaging.

Any suitable packaging may be used and will depend on the exact nature of the product.

The product of the second aspect may include instructions for use. These may be provided on the packaging.

Other preferred features of the second aspect are as described in relation to the first aspect.

The composition of the present invention may be prepared by any suitable means. Such means will be known to the person skilled in the art and include, for example, forming a melt of the constituent components, pouring the melt into a mould and allowing it to set.

However in preferred embodiments the composition is prepared by admixing the solid components and then compacting to form the desired product shape.

Suitably the composition is prepared by admixing the components in particulate form, pouring the mixed particulates into a mould and then compacting in the mould. The size of particulate may be selected to give the desired properties of the product.

Such a cold pressing method is advantageous over a melt method as less energy is used.

According to a third aspect of the present invention there is provided a method of treating the hair and/or skin, the method comprising contacting the hair and/or skin with a composition of the first aspect and then rinsing the composition from the hair and/or skin with water.

The method of the third aspect may suitably involve wetting the hair and/or skin and/or wetting the solid composition with water prior to contacting the composition with the hair and/or skin.

Preferably the method is a method of washing the hair and/or skin. Preferably it is a method of treating the hair.

Preferred features of the third aspect are as defined in relation to the first aspect.

The invention will now be further defined with reference to the following non-limiting examples.

EXAMPLES

Solid Shampoo Bars were prepared comprising the following ingredients:

|  | Product A | Product B | Product C | Product D |
|---|---|---|---|---|
| Iselux ® Flakes (1) | 93.5 wt % |  |  | 46.75 wt % |
| Pureact I-78C (2) |  | 93.5 wt % |  |  |
| SLS (3) |  |  | 93.5 wt % | 46.75 wt % |
| CAPB (4) |  |  | 3% wt |  |
| Pureact WS Conc (5) |  |  | 2% wt |  |
| Natrlquest ® E30 (6) |  |  | 1% wt |  |
| Condicare PQ 7 (7) |  |  | 0.5% wt |  |

(1) Iselux ® Flakes was provided as solid flakes comprising approximately 80% sodium lauroyl methyl isethionate together with lauric acid, laurate salts and sodium methyl isethionate
(2) Pureact I-78C was provided as noodles comprising 80-82% sodium cocoyl isethionate, and 10-12% fatty acids and sodium isethionate.
(3) SLS was provided as needles comprising approximately 92% sodium lauryl sulfate.
(4) CAPB was provided as an aqueous solution comprising 30% of cocamidopropyl betaine.
(5) Pureact WS Conc was provided as an aqueous solution comprising 30% sodium methyl cocoyl taurate
(6) Natrlquest ® E30 was provided as an aqueous solution comprising 37% tri sodium ethylene diamine disuccinate.
(7) Condicare PQ 7 was provided as an aqueous solution comprising 10% of polyquaternium 7, a copolymer of acrylamide and diallyldimethyl ammonium chloride The compositions were prepared by the following method:

1. In a well ventilated area flakes of Sodium Lauroyl Methyl Isethionate were ground to a fine power. This provides a smooth bar effect. Small chunks may be used for a mottled effect.

2. All other ingredients were mixed together in a separate beaker. Colour and fragrance may be added at this stage.

3. The powder obtained in step 1 was added to the mixture obtained in step 2 and the mixture was stirred well until the powder was completely coated. This was then added to a mould and compacted at room temperature using a press at 40-60 P.S.I.

Each composition was then assessed by a panel.

The panel members used each of the compositions to wash their hair according to the method described in table 1. The panel was asked to evaluate the products with reference to the foaming and rinsing of the product and shine, softness and combability of the hair after use. The results are shown in table 2.

TABLE 1

Preparation of Hair

| | |
|---|---|
| 1. | Rinse hair with warm water |
| 2. | Wet shampoo bar with warm water and apply three strokes to wet hair |
| 3. | Lather into the hair and assess foam characteristics of shampoo (0 = poor foaming, 5 = good foaming) |
| 4. | Rinse with warm water and assess how long it takes (0 = long, 5 = short) |
| 5. | Blow dry until dry |
| 6. | Assess combability (0 = hard, 5 = easy) |
| 7. | Assess softness of hair (0 = not soft, 5 = soft) |
| 8. | Assess shine of hair (0 = dull, 5 = shine) |

TABLE 2

Shampoo Bar Sensory Testing Results

| | Product A | Product B | Product C | Product D |
|---|---|---|---|---|
| Foam | 4.5 | 3.75 | 4.25 | 4.5 |
| Rinse | 2.75 | 2.5 | 2.5 | 2.5 |
| Shine | 3.25 | 2.5 | 2.5 | 2.75 |
| Softness | 3.25 | 2.5 | 2.5 | 2.75 |
| Combability | 2.25 | 2 | 2 | 2.25 |
| Total | 16 | 13.25 | 13.75 | 14.75 |
| Mean | 3.2 | 2.65 | 2.75 | 2.95 |

Composition A was observed to provide the best foam volume, combability, hair softness, shine and rinse overall.

Additional Examples

Further examples of solid shampoo bars according to the invention were prepared in a similar manner to the previous examples.

| | Amount/% w/w | | |
|---|---|---|---|
| Ingredients | Hair Conditioning Shampoo Bar | Anti-Dandruff Hair Shampoo Bar (1) | Anti-Dandruff Hair Shampoo Bar (2) |
| Iselux | 90.20 | 93.00 | 93.00 |
| Cocamidopropyl Betaine | 3.00 | 3.50 | 3.00 |
| Pureact WS Conc | 2.00 | 2.00 | 2.00 |
| Natrlquest E30 | 1.00 | — | 1.00 |
| Condicare PQ7 | 0.50 | 0.50 | 0.50 |
| Zinc Pyrithione (8) | — | 1.00 | — |
| Piroctone Olamine (9) | — | — | 0.5 |
| Dimethicone (10) | 3.00 | — | — |
| Activsoft C13 (11) | 0.30 | — | — |

(8) Approximately 98% active Zinc Pyrithione (bis(2-Pyridylthio)zinc 1,1'-dioxide), an anti-dandruff agent, was provided as a powder.

(9) Approximately 98% active Piroctone Olamine (1-Hydroxy-4-methyl-6-(2,4,4-trimethylpentyl)-2-(1H)pyridinone,2-aminoethanol salt), an anti-dandruff agent, was provided as a crystalline powder.

(10) Dimethicone (Polydimethylsiloxane), a hair conditioning agent, was provided as a viscous liquid with a viscosity of 60,000 cSt.

(11) Activsoft C13 (a cationically derivatised galactomannan gum), a hair conditioning agent and dimethicone deposition aid was provided as a powder.

These shampoo bars were found to have good integrity and excellent foaming properties.

The invention claimed is:

1. A solid personal care foamable shampoo composition comprising at least 65 wt % of one or more solid surfactants of which at least 90 wt % comprises one or more compounds of formula (I):

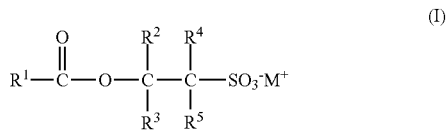

wherein $R^1$ represents a $C_7$ to $C_{21}$ alkyl;
each of $R^2$, $R^3$, $R^4$ and $R^5$ independently represents a hydrogen atom or a $C_{1-4}$ alkyl group and
wherein at least one of $R^2$, $R^3$, $R^4$ and $R^5$ is not hydrogen; and M+ represents sodium, zinc, potassium or ammonium; and
wherein the composition comprises less than 5 wt % of traditional soap compounds.

2. The composition according to claim 1 wherein one or more compounds of formula (I) is selected from sodium lauroyl methyl isethionate, sodium cocoyl methyl isethionate, sodium oleoyl methyl isethionate and mixtures and/or isomers thereof.

3. The composition according to claim 1 wherein the compound of formula (I) comprises a mixture of isomers including a compound of formula $R^1COOCH_2CHR^4SO_3^- M^+$ in which $R^4$ is $C_1$ to $C_4$ alkyl and a compound of formula $R^1COOCHR^2CH_2SO_3^- M^+$ in which $R^2$ is $C_1$ to $C_4$ alkyl.

4. The composition according to claim 1 which further comprises one or more surfactants selected from anionic surfactants, cationic surfactants, nonionic surfactants and amphoteric surfactants.

5. The composition according to claim 1 which further includes one or more ingredients selected from fragrances, dyes, structuring aids, fillers, pH adjustment agents, chelating agents, antidandruff agents and conditioning agents.

6. A personal care product comprising the composition according to claim 1 and packaging.

7. The composition according to claim 1 which comprises at least 80 wt % solid surfactants.

8. The composition according to claim 1 wherein at least 95 wt % of the solid surfactants present in the composition comprise one or more compounds of formula (I).

9. The composition according to claim 1 which further comprises from 0.1 to 10 wt % of a betaine surfactant.

10. The composition according to claim 1 which further comprises from 0.1 to 10 wt % of a taurate surfactant.

11. The composition according to claim 1 which comprises at least 70 wt % solid surfactants.

12. The composition according to claim 11 wherein at least 95 wt % of the solid surfactants present in the composition comprise one or more compounds of formula (I).

13. The composition according to claim 1 which comprises 75 wt % solid surfactants.

14. The composition according to claim 13 wherein at least 95 wt % of the solid surfactants present in the composition comprise one or more compounds of formula (I).

* * * * *